United States Patent [19]
Goldrath

[11] Patent Number: 5,437,629
[45] Date of Patent: Aug. 1, 1995

[54] FLUID DELIVERY SYSTEM FOR HYSTEROSCOPIC ENDOMETRIAL ABLATION

[75] Inventor: Milton H. Goldrath, Franklin, Mich.

[73] Assignee: BEI Medical Systems, Hackensack, N.J.

[21] Appl. No.: 227,724

[22] Filed: Apr. 14, 1994

[51] Int. Cl.⁶ ............................................. A61M 3/04
[52] U.S. Cl. ........................................ 604/21; 604/28; 604/55; 606/27; 606/96; 128/766
[58] Field of Search ............................. 604/21, 27–28, 604/55, 96; 606/27–28, 96, 113–114, 191–192; 607/105; 128/4, 736, 766

[56] References Cited

U.S. PATENT DOCUMENTS

| | | |
|---|---|---|
| 3,850,162 | 11/1974 | Iglesias . |
| 3,924,628 | 12/1975 | Droegemueller et al. . |
| 4,071,027 | 1/1978 | Meador . |
| 4,637,814 | 1/1987 | Leiboff . |
| 4,795,424 | 1/1989 | Burner . |
| 4,949,718 | 8/1990 | Neuwirth et al. . |
| 4,955,391 | 9/1990 | Parker et al. . |
| 5,084,044 | 1/1992 | Quint . |
| 5,147,353 | 9/1992 | Everett . |
| 5,242,390 | 9/1993 | Goldrath . |
| 5,242,437 | 9/1993 | Everett et al. . |
| 5,248,312 | 9/1993 | Lanberg . |
| 5,277,201 | 1/1994 | Stern . |
| 5,300,023 | 4/1994 | Lowery et al. . |
| 5,320,091 | 6/1994 | Grossi et al. . |
| 5,380,317 | 1/1995 | Everett et al. . |

*Primary Examiner*—C. Fred Rosenbaum
*Assistant Examiner*—Perry E. Van Over
*Attorney, Agent, or Firm*—Gifford, Krass, Groh, Sprinkle, Patmore, Anderson & Citkowski

[57] ABSTRACT

Apparatus for and method of recirculating fluid used in performing hysteroscopic endometrial ablation. The fluid preferably circulates through a closed loop, fluid delivery system, including a heater for heating the fluid, and passes through a chamber of known volume having graduated markings disposed thereon so that the amount of fluid circulating within the closed loop system can be continuously monitored. The apparatus is connected to the inlet and outlet ports of a hysteroscopic sheath positioned within the uterine cavity of a patient. Any drop of fluid level within the marked chamber will indicate to the surgeon that the patient is undesirably absorbing fluid so that the procedure may be swiftly terminated before adverse consequences occur.

17 Claims, 2 Drawing Sheets

FLUID DELIVERY SYSTEM FOR HYSTEROSCOPIC ENDOMETRIAL ABLATION

FIELD OF THE INVENTION

The present invention concerns the field of hysteroscopic endometrial ablation performed using a heated fluid and, more particularly, to a system for delivering said heated fluid.

BACKGROUND OF THE INVENTION

U.S. Pat. No. 5,242,390 discloses a method and apparatus for thermally ablating the lining of the uterus (known as the endometrium). The patented apparatus comprises a hysteroscope having a proximal portion for insertion into the uterus through the vagina, and a distal, gripping, visualization portion. The hysteroscope comprises both optical means for viewing the uterine cavity and channel means for delivering tissue-coagulating, controllably heated liquid into the cavity, as well as thermal insulation means for the hysteroscope. The thermal insulation means insulates the other body structures from the potentially damaging heat of the liquid during the period of the heated liquid transport and the coagulating surgery with the liquid so as to avoid thermal damage to tissue other than the endometrial tissue (such as vaginal tissue and endocervical tissue). The apparatus also includes liquid supply means for transporting the liquid through the channel means into and from the uterine cavity, and control means for regulating the temperature and pressure of the heated liquid.

The method of the patent as described therein includes the steps of: (a) distending the uterine cavity with a physiologically compatible aqueous solution (such as saline solution or other suitable liquid) under direct vision by means a hysteroscope having channel means for delivering and introducing liquid to the uterine cavity under pressure sufficient to inflate and directly expose the entire endometrial surface; (b) confirming that the proximal portion of the hysteroscope is properly located within the uterine cavity by appropriate visualization of its internal architecture; (c) withdrawing the aqueous solution from the uterine cavity, thus causing it to become substantially collapsed; and (d) distending the thus collapsed uterine cavity under direct vision by means of said hysteroscope by delivering and introducing to the uterine cavity aqueous carbohydrate solution (or a suitable equivalent solution) heated to an endometrial tissue-coagulating temperature under pressure sufficient to directly expose the entire endometrial surface and for a time sufficient to keep the heated solution in contact with the entire surface and, thereby, cause uniform and complete destruction of the endometrium.

The patent discloses a liquid supply means to the hysteroscope in the form of a syringe barrel and plunger containing heated liquid which is manually injected into the inlet port of the hysteroscopic sheath. The fluid which exits out of the uterine cavity and back through said channel and port of the sheath is circulated into a waste reservoir. Optionally, a separate supply of cold liquid is available, also in the form of a syringe barrel and plunger. Various valves are disclosed to control the ingress and egress of the various liquids.

Certain problems can arise during such surgical procedures, particularly if the patient absorbs a quantity of the heated liquid into her circulation (or fallopian tubes) during the installation of the heated solutions. During other types of hysteroscopic procedures, patients have been known to absorb large quantities of the liquid (as much as 2,000 or 3,000 cc) which can cause serious complications, up to and including death. Obviously, it is extremely important to closely monitor the amount of liquid being used to perform the procedure in order to ensure that no significant amounts are being absorbed. The fluid delivery system disclosed in U.S. Pat. No. 5,242,390 does not really provide any practical way of performing such monitoring.

SUMMARY OF THE INVENTION

The present invention has been designed to overcome the prior art deficiencies noted above. Accordingly, the invention provides a system for, and method of, delivering liquid used to perform hysteroscopic endometrial ablation (or other hysteroscopic procedures involving the uterine cavity) wherein the amount of liquid in use can be closely monitored at all times.

In its broadest aspect, the invention included first and second fluid conduits for, respectively, delivering and drawing away physiologically compatible fluid into and out of the uterine cavity of a patient. The first conduit delivers a first stream of fluid of a known magnitude (by "magnitude" is meant flow rate, pressure, volume, or any other measurable quality that reflects the quantity of fluid being introduced). The system also includes means for measuring the magnitude of a second stream of fluid exiting the uterine cavity via the second conduit and for determining a differential between the magnitude of the second stream and the known magnitude of the first stream. Means are provided for terminating the flow of said first stream when the measured differential exceeds a preset value; e.g., the amount of fluid leaving the uterus is less than the amount entering by more than a selected value, thus indicating the patient is absorbing too much fluid. The preset value will reflect the type of procedure being performed. The system may also include means for heating the first stream of fluid.

In a preferred embodiment, the apparatus is a closed loop conduit system which recirculates and heats the liquid. Disposed within the circulation loop of the system is a chamber, preferably with volume level markings indicated thereon. Close monitoring of the level of the liquid in the chamber will reveal whether any of the recirculating fluid is being absorbed by the patient. If the fluid level drops within the chamber, then the circulation of fluid through the closed loop can be immediately cut off and the procedure terminated before the patient has absorbed any harmful quantities. Preferably, the chamber may include a sensor for determining whether the fluid level has fallen below a preset minimum and a switch associated therewith for cutting off power to the system.

In a preferred embodiment of the apparatus of the present invention, the fluid chamber is in fluid communication with a supply of a physiologically compatible aqueous-solution (such as is described in the above-referenced '390 patent, the disclosure of which is hereby incorporated by reference). A first pinch valve controls the flow of solution between the source and the chamber. Disposed in the system downstream of the chamber is a heater through which the circulating solution passes for heating to an effective temperature; preferably a temperature monitor is operatively associated with the heater to keep the circulating solution at the desired temperature. The heater is in fluid communication (preferably via an insulated conduit) with the inlet port of a hysteroscopic sheath used to perform the thermal ablation procedure so that heated solution is introduced into the sheath and, subsequently, into the uterine cavity of a patient. Fluid exiting from the uterine cavity and sheath via the sheath's exit port is then circulated via the closed loop, by a peristaltic pump. Preferably, the closed loop is also formed of insulated tubing. Optionally, the source of solution and chamber may be located above the level of the patient (preferably three to four feet), and the peristaltic pump may be located at or below the level of the patient. Optionally, a portion of the recirculating apparatus may be disposed at an even lower level so that fluid exiting from the sheath will gravity drain and collect before entering the pump. A second, lower chamber may be disposed at this point for collection of the solution.

The peristaltic pump is in fluid communication with the upper chamber so that circulating solution may be pumped against gravity and back into the chamber. A collection bottle is also in fluid communication with the closed loop system for collection of the priming fluid until the loop is closed. Second and third pinch valves are disposed, respectively, between the peristaltic pump and the upper chamber and the collection bottle and the closed loop. Also, the fluid chamber includes an air valve which is opened and closed by means of a fourth pinch valve.

BRIEF DESCRIPTION OF THE DRAWINGS

The following detailed description is best understood by reference to the drawings in which.

DETAILED DESCRIPTION OF THE PREFERRED EMBODIMENTS

Figure 1:
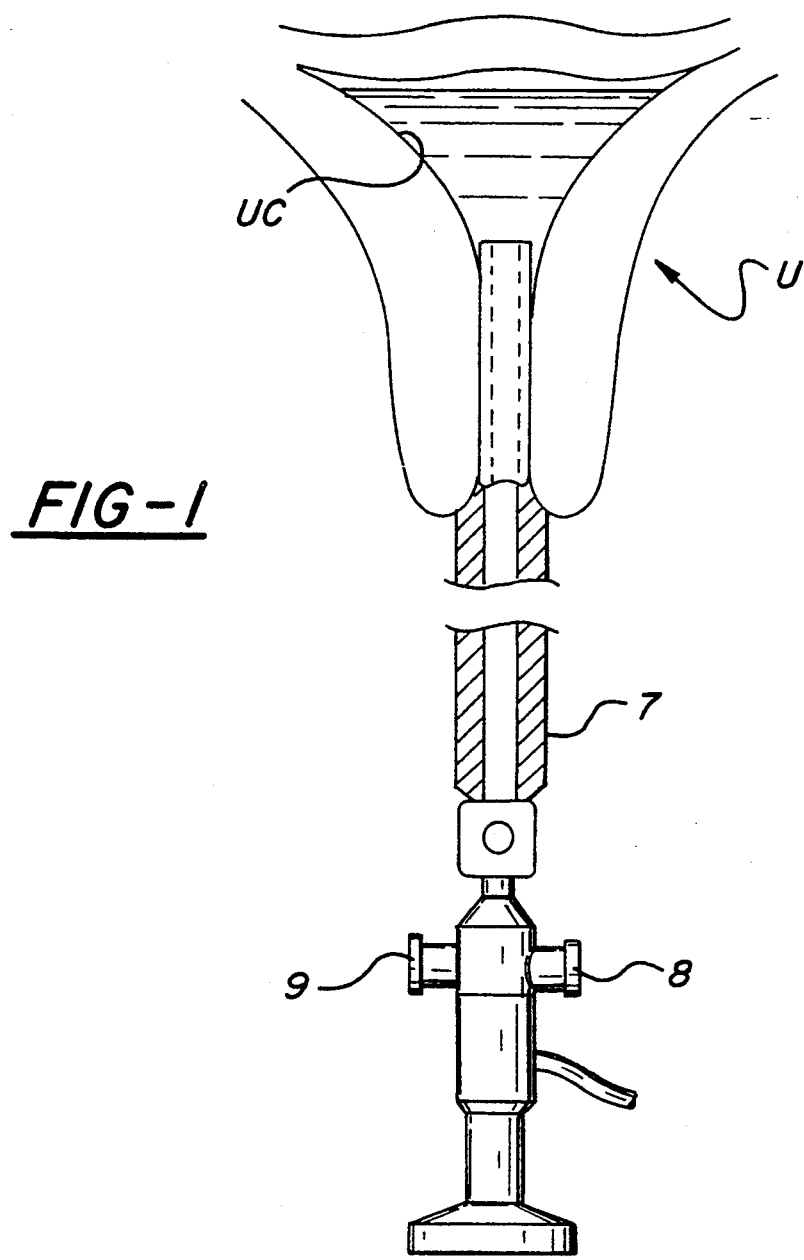
FIG. 1 is a schematic view of a hysteroscopic sheath used to perform thermal ablation of the endometrium, said sheath being supplied with an inlet port and an outlet port.

Throughout the following detailed description, like numerals are used to reference the same element of the present invention shown in multiple figures thereof. Referring now to FIG. 1 there is shown a hysteroscopic sheath 7 suitable for practicing thermal endometrial ablation surgery. Details of the sheath 7 are disclosed in U.S. Pat. No. 5,242,390 and will not be discussed in detail. Suffice it to say that a flow of heated, biologically compatible aqueous solution is delivered into the sheath 7 via inlet port 8. It then flows through the sheath 8 and into the cavity UC of the uterus U to contact the entire surface of the endometrial lining. Fluid from the uterine cavity UC then returns via the hysteroscopic sheath 7, (the fluid flow channels are not shown; reference is had to the '390 patent for a more complete description) and exits the sheath 7 via the exit port 9.

Figure 2:
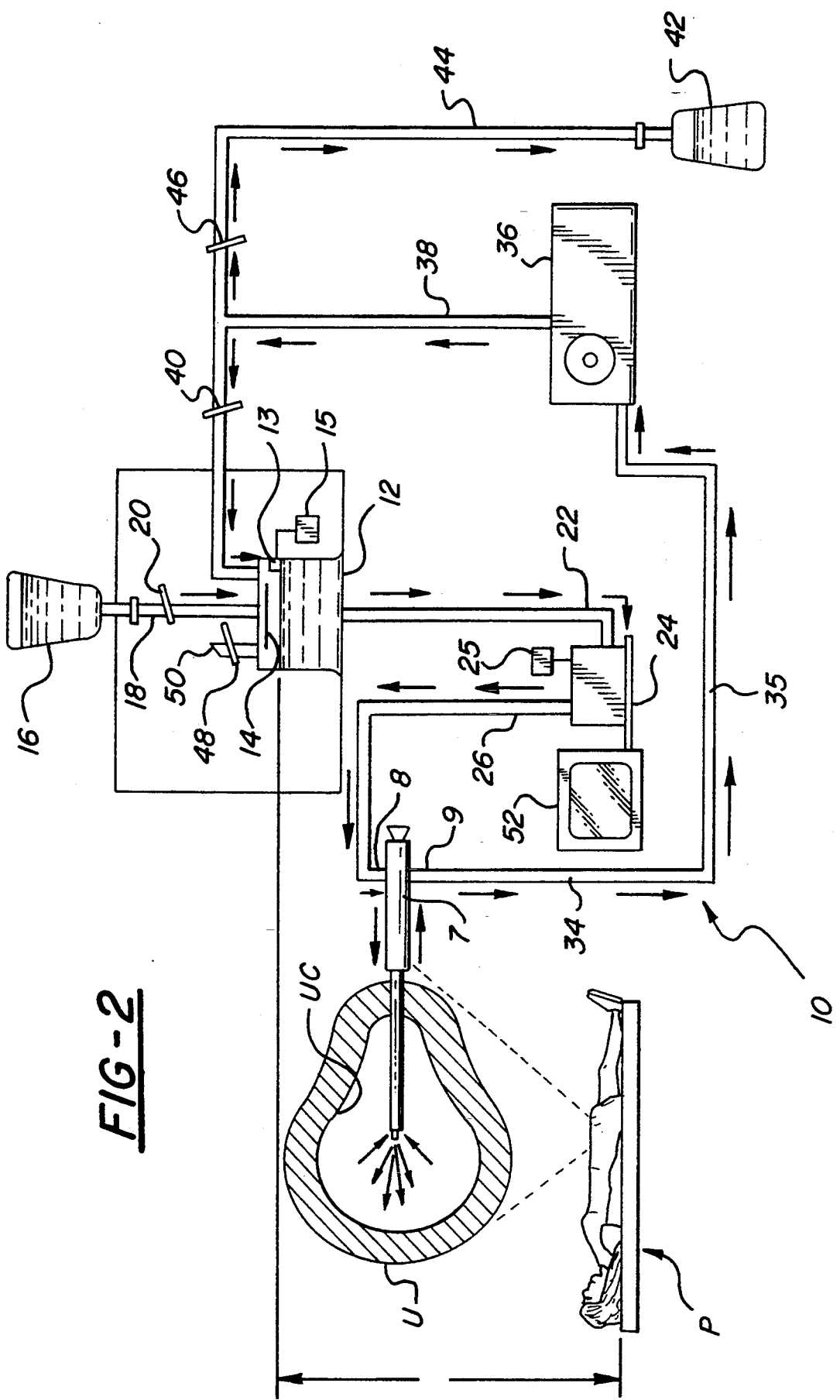
FIG. 2 is a schematic diagram of a closed loop embodiment of the system of the present invention for supplying heated liquid to the hysteroscopic sheath of FIG. 1.

FIG. 2 depicts in schematic form such a hysteroscopic sheath 7 in use on a patient P, upon whom thermal ablation of the endometrium is being performed. The present invention includes an apparatus 10 for recirculating and heating a quantity of a aqueous physiologically compatible solution. In FIG. 2, the arrows show the direction of fluid flow through the various elements of the system 10. The system includes a chamber 12 having indicia markings 14 thereon for indicating the level of fluid contained therein. A source 16 of the physiologically compatible solution is in fluid communication with chamber 14 by way of tube 18. A first pinch valve 20 controls the flow of fluid between the source 16 and the chamber 14. Chamber 14 is also in fluid communication via conduit 22 with a heater 24 through which the fluid flows and is heated. Preferably, a monitor 52 is operatively associated with the heater so that the temperature of the fluid can be continuously monitored and adjusted accordingly. An insulated inlet tube 26 places heater 24 and hysteroscopic sheath 7 in fluid communication. The inlet tube 26 is connected to the inlet port 8 of the sheath 7. The heated fluid then flows through the sheath 7 and into the uterine cavity UC. Fluid from the uterine cavity UC flows back through the sheath 7, out the exit port 9 and into an insulated outlet tube 34 so as to subsequently collect in a collection tube 35 which is in fluid communication with a pumping means 36, such as a peristaltic pump. Peristaltic pump 36 serves to pump the circulating fluid upward, against gravity, through conduit 38 which is in fluid communication with the chamber 12 to close the system loop. A second pinch valve 40 controls the flow of fluid between pump 36 and chamber 12. A collection bottle 42 is also in fluid communication with conduit 38 by means of tube 44. A third pinch valve 46 controls the flow of fluid between the collection bottle and the rest of the system 10. As the direction of the arrows indicate, fluid flows from the source 16 into the system, whereas it flows from the system 10 to the collection bottle 42.

The recirculating system 10 operates as follows: the system 10 is primed by opening the fluid source 16 preferably a plastic bag containing a 0.9% saline solution, so that fluid empties into the chamber 14 via tube 18. Chamber 12 preferably has a volume somewhere between 50 and 75 cc, and the indicia markings 16 thereon are graduated in 1-2 cc increments. Initially, the air vent 50 in the chamber 12 is closed by means of fourth pinch valve 48, as is the second pinch valve 40 which controls the flow of fluid into the chamber 14 from the pump 36. However, the first pinch valve 20 from fluid source 16 is open. The recirculating solution initially partially fills the upper chamber, and then proceeds to fill the conduit 22 leading to the heater 24. After heater 24 fills up, the fluid flows through inlet tube 26 and inlet port 8 to fill hysteroscopic sheath 7 and circulate into the uterine cavity UC. The fluid then exits back into the sheath 7 and out through the outlet port 9 so as to drain through outlet tube 34 into collection tube 35. The fluid collects in collection tube 35 and is sucked from the tube 35 by pump 36 and recirculates back toward the chamber 12. During the priming process, third pinch valve 46 between the collection bottle 42 and the system 10 is open so that all fluid will flow into prime bottle 42.

When the system 10 is totally filled with the saline solution and the surgeon assures himself that he has a good and clear view of the uterine cavity UC, third pinch valve 46 is closed so that fluid will no longer flow into the collection bottle 42. The second pinch valve 40 between the pump 36 and the chamber 12 is opened. The first pinch valve from the source bottle 16 is closed, whereas the fourth pinch valve 48 controlling the air valve 50 of chamber 12 is opened. Preferably, pinch valves 46 and 20 are closed and the pinch valves 40 and 48 are opened in one mechanical operation by using a rotary type valve. Optionally, a switch 25 for heater 24 may be provided on the rotary valve so that the heater 24 operates only during circulation of fluid as a safety precaution. Air vent 50 is necessary so that the pump 36 will not increase the pressure within the system by compressing air.

After pinch valves 20 and 46 are closed and pinch valve 40 is opened, the fluid will continuously circulate through the various elements of the system 10 as long as the pump 36 continues to operate. Chamber 14 provides a convenient way of optically monitoring the amount of fluid circulating through the system 10. However, the embodiment depicted in FIG. 2 also includes a sensor 13 disposed in chamber 12 for sensing whether fluid within chamber 12 has fallen below a pre-set, minimum level. Switch 15 is in communication with sensor 13 and automatically cuts off power to the system 10 upon receiving a signal from sensor 13. As long as the fluid in the chamber 12 remains constant, the surgeon knows that none of the fluid is escaping, either by leaking or by absorption into the patient's circulation. It is possible that leaks could occur around the cervix, but this could be corrected during the priming stage by putting in an appropriate clamp upon the cervix. Assuming that there is no actual leakage, any decrease of volume in the upper chamber 12 during performance of the ablation procedure would of necessity be caused by fluid flowing into the patient's circulation, or perhaps through the fallopian tubes. Thus, if the fluid level in chamber 14 begins to fall during the procedure, it will be automatically and immediately terminated so as to prevent any further absorption of fluid.

Figure 3:
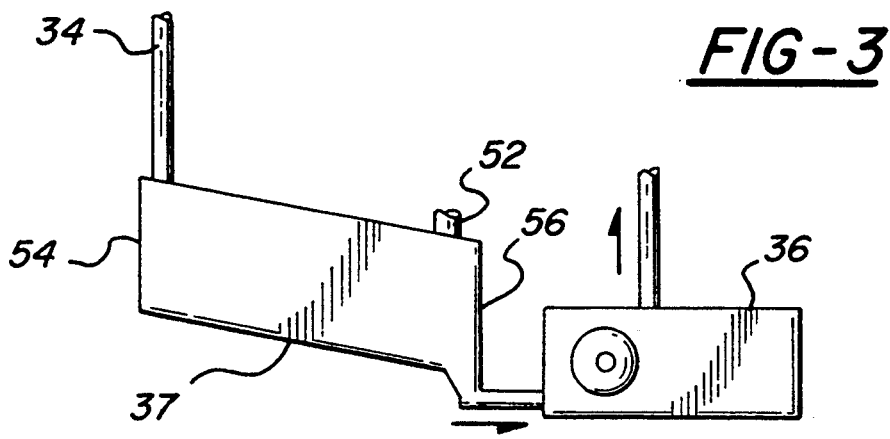
FIG. 3 is a schematic view of the lower portion of the closed loop system of an alternate embodiment.

FIG. 3 depicts an alternate embodiment of the lower part of the system 10. In this embodiment, outlet tube 34 connects to a second, lower chamber 37 being provided with an air vent 52. In this embodiment, the fluid exiting from the sheath 7 gravity drains into lower chamber 37 and is subsequently pumped out by pump 36. To assist in gravity drainage, one end 54 of chamber 37 (closest to the outlet tube) is preferably higher than the other end 56 closest the pump 36. Air vent 52 always remains open.

It should be noted that the maximum pressure obtainable in the system of FIG. 3 is the head of pressure from the fluid level in the chamber 12 to the level of the patient P which is, preferably, three or four feet. No further pressurization of the system is required.

Thus, the apparatus and method of the present invention provide a mechanically simple, elegant and reliable way of recirculating heated fluid used in the ablation procedure, while at the same time continuously monitoring the system for a sudden and undesirable drop in fluid level. Of course, while the system is illustrated for delivery of saline solution, it can also be used to deliver any other physiologically compatible fluid necessary to perform the procedure, as well as to deliver both cool and heated fluid as required simply by using or not using the heater. Thus, all of the fluid used in the surgical method disclosed in U.S. Pat. No. 5,242,390 may be delivered by the recirculating system of the present invention.

While the present invention has been described with reference to certain embodiments and exemplifications therein, it is not limited to the exact designs depicted. Certain variations in the method and apparatus of the present invention may occur to one skilled in the art having had the benefit of the teachings of the present disclosure. For example, the exact arrangement and components of the depicted system may not be necessary to practice the present invention, but may be further modified and varied as required without departing from the scope thereof. It is the claims appended hereto, and all reasonable equivalents thereof, which define the scope of the present invention.

I claim:

1. A fluid delivery apparatus for use in performing hysteroscopic endometrial ablation, said system comprising:
   a chamber of known volume having graduated markings indicative of a plurality of fluid levels;
   a container of physiologically compatible solution in fluid communication with said chamber;
   a first valve for controlling the flow of physiologically compatible solution into said chamber from said container;
   a heater disposed downstream of said chamber for heating a flow of fluid passing therethrough;
   a first conduit disposed between said chamber and said heater;
   a hysteroscopic sheath capable of introducing heated physiologically compatible solution into the uterine cavity of a patient and being provided with an inlet port and an outlet port;
   a fill tube connecting said heater and said sheath inlet port;
   a discharge tube from said sheath outlet port;
   collection means connected to said discharge tube such that fluid discharged from said sheath collects therein;
   fluid pumping means in fluid communication with said collection means;
   a second conduit between said pump and said chamber to form a closed loop circulation system;
   a collection bottle containing a quantity of physiologically compatible solution disposed in fluid communication with said second conduit;
   a second valve disposed in said second conduit between said collection bottle and said chamber for controlling the flow of fluid into said chamber; and
   a third valve for controlling the flow of fluid from said collection bottle into said second conduit.

2. The system of claim 1 further comprising a temperature monitor disposed in operative association with said heater for monitoring the temperature of fluid flowing into said hysteroscopic sheath.

3. The system of claim 1 wherein said fluid pumping means is a peristaltic pump.

4. The system of claim 1 wherein said collection means is a second chamber angles downwardly from an upper end disposed proximate said discharge tube to a lower end proximate said pumping means.

5. The system of claim 4 wherein said chamber is disposed three to four feet above the level of said patient.

6. The system of claim 1 wherein said chamber is provided with an air valve.

7. The system of claim 6 wherein said air valve and said first, second and third valve comprise a single rotary valve for synchronous operation.

8. The system of claim 1 wherein said first and second conduits, said fill and discharge tubes and said collection means is formed of insulated tubing.

9. The system of claim 1 further including a sensor disposed in said chamber for sensing the level of fluid therewithin and producing a signal when said fluid level falls below a preset minimum.

10. The system of claim 9 further comprising a switch in communication with said sensor for receiving said signal and terminating operation of said system.

11. A method of recirculating and heating fluid used in performing hysteroscopic endometrial ablation, said method comprising:

providing a recirculating system including:

a chamber of known volume having graduated markings indicative of a plurality of fluid levels, said chamber being provided with an air valve;

a container of physiologically compatible solution in fluid communication with said chamber;

a first valve for controlling the flow of physiologically compatible solution into said chamber from said container;

a heater disposed downstream of said chamber for heating a flow of fluid passing therethrough;

a first conduit disposed between said upper chamber and said heater;

a hysteroscopic sheath capable of introducing heated physiologically compatible solution into the uterine cavity of a patient and being provided with an inlet port and an outlet port;

a fill tube connecting said heater and said sheath inlet port;

a discharge tube from said sheath outlet port;

collection means connected to said discharge tube such that fluid discharged from said sheath collects therein;

fluid pumping means in fluid communication with said collection means;

a second conduit between said pump and said chamber to form a closed loop circulation system;

a collection bottle containing a quantity of physiologically compatible solution disposed in fluid communication with said second conduit;

a second valve disposed in said second conduit between said collection bottle and said chamber for controlling the flow of fluid into said chamber; and a third valve for controlling the flow of fluid from said collection bottle into said second conduit;

closing said air valve in said chamber and said second valve, and opening said first and third valves;

allowing physiologically compatible solution to flow from said container into said chamber, said first conduit, and said heater;

operating said heater to heat solution flowing therethrough;

allowing said heated solution to fill said hysteroscopic sheath and circulate into said uterine cavity, and exit through said outlet port;

allowing said discharged solution to drain into said collection means so that it is collected therein;

operating said pumping means to draw said collected fluid from said collection means and pump it into said second conduit;

allowing said pumped liquid to flow into said collection bottle until said system and said uterine cavity are totally filled with said physiologically compatible solution; and closing said first and third valves and opening said second valve and said air valve in said chamber to allow pumped solution to flow into said chamber for subsequent recirculation through said system.

12. The method of claim 11 comprising the further step of monitoring the level of liquid in said chamber to assure that said level remains relatively constant.

13. The method of claim 12 comprising the further step of stopping the circulation of solution through the system when the level of solution in said upper chamber begins to decline so as to prevent absorption of said solution by said patient.

14. A system for recirculating physiologically compatible solution used in performing hysteroscopic endometrial ablation, said system comprising:

a fluid conduit having a first end and a second end, said first end being attached to an inlet port of a hysteroscopic sheath and said second end being attached to an outlet port of said hysteroscopic sheath to form a closed loop fluid system;

a source of physiologically compatible solution;

a chamber for containing a portion of said physiologically compatible solution in fluid communication with said source and with said conduit at a location upstream of said hysteroscopic sheath;

a heater disposed in said conduit medial said chamber and said sheath;

a pumping means disposed in said conduit downstream of said sheath;

a collection bottle in fluid communication with said conduit at a location medial of said pumping means and said chamber; and first, second and third valve means for controlling, respectively, fluid flow between said source and said chamber, said pump and said chamber, and said collection bottle and said conduit.

15. The system of claim 14 wherein said fluid conduit is formed of insulated tubing.

16. A fluid delivery system for use in hysteroscopic procedures requiring the delivery of a fluid to the uterine cavity of a patient, said system comprising:

a first conduit for introducing a first stream of physiologically compatible fluid of a known magnitude into a uterine cavity of a patient;

a second conduit for drawing away a second stream of said fluid from said uterine cavity;

means for measuring the magnitude of said second stream of fluid and determining a differential between said magnitude of said second stream and said known magnitude of said first stream; and means for terminating the flow of said first stream when said differential exceeds a preset value.

17. The system of claim 16 further comprising means for heating the first stream of liquid.

* * * * *